United States Patent
Burton

(10) Patent No.: US 8,116,554 B2
(45) Date of Patent: Feb. 14, 2012

(54) TWO COLOUR VISION SYSTEM

(75) Inventor: Colin Michael Burton, Norwich (GB)

(73) Assignee: AEW Delford Systems Limited (GB)

( * ) Notice: Subject to any disclaimer, the term of this patent is extended or adjusted under 35 U.S.C. 154(b) by 909 days.

(21) Appl. No.: 11/917,880

(22) PCT Filed: Jun. 21, 2006

(86) PCT No.: PCT/GB2006/002270
§ 371 (c)(1),
(2), (4) Date: May 7, 2008

(87) PCT Pub. No.: WO2006/136818
PCT Pub. Date: Dec. 28, 2006

(65) Prior Publication Data
US 2008/0212842 A1    Sep. 4, 2008

(30) Foreign Application Priority Data

Jun. 24, 2005 (GB) .................................... 0512877.2
Sep. 1, 2005 (GB) .................................... 0517734.0

(51) Int. Cl.
*G06K 9/00* (2006.01)

(52) U.S. Cl. ........................................................ 382/141
(58) Field of Classification Search ........................ None
See application file for complete search history.

(56) References Cited

U.S. PATENT DOCUMENTS
2005/0120844 A1 * 6/2005 Weber .............................. 83/35

FOREIGN PATENT DOCUMENTS
DE         101 36 809 A1 *   2/2003
* cited by examiner

*Primary Examiner* — Tu Nguyen
(74) *Attorney, Agent, or Firm* — Barnes & Thornburg LLP

(57) ABSTRACT

A vision system for viewing the end face of product mounted in a machine which in use produces measurements relating to the area of the end face and of at least one constituent part of the product which is visible in the end face. The end face is illuminated by light of two different wavelengths. One wavelength illuminates an area which contains both the end face and surrounding parts of the machine, while light of the other wavelength from a laser source produces a pattern of parallel spaced apart lines of light of the other wavelength. The parallel lines cross the end face at a specific given angle. Gating excludes video signal of parallel lines in the image which are not at the specific angle to leave a residual video signal corresponding to the end face. A full color video signal of the field of view is gated by the mask.

15 Claims, 13 Drawing Sheets

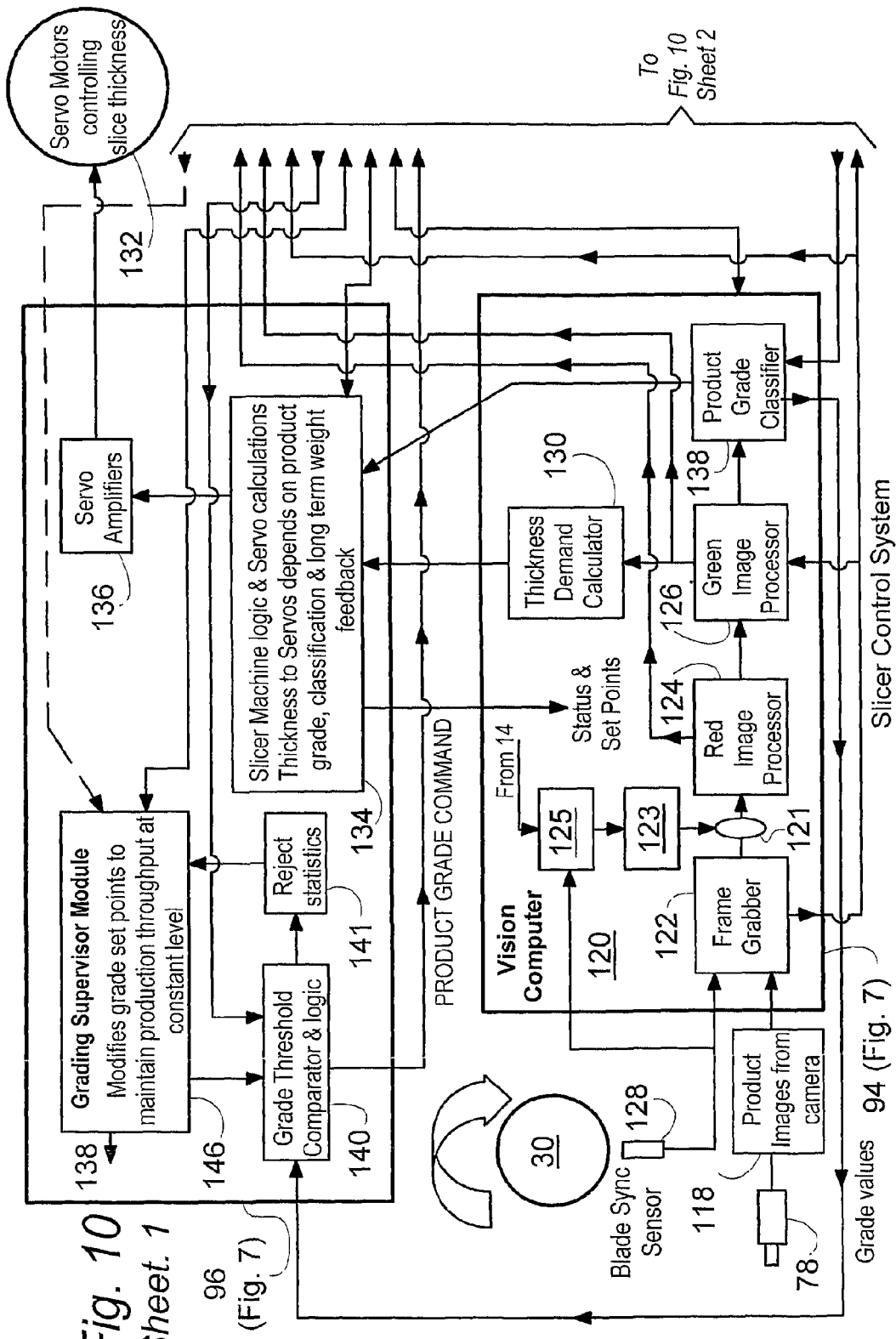
Fig. 10 Sheet. 1

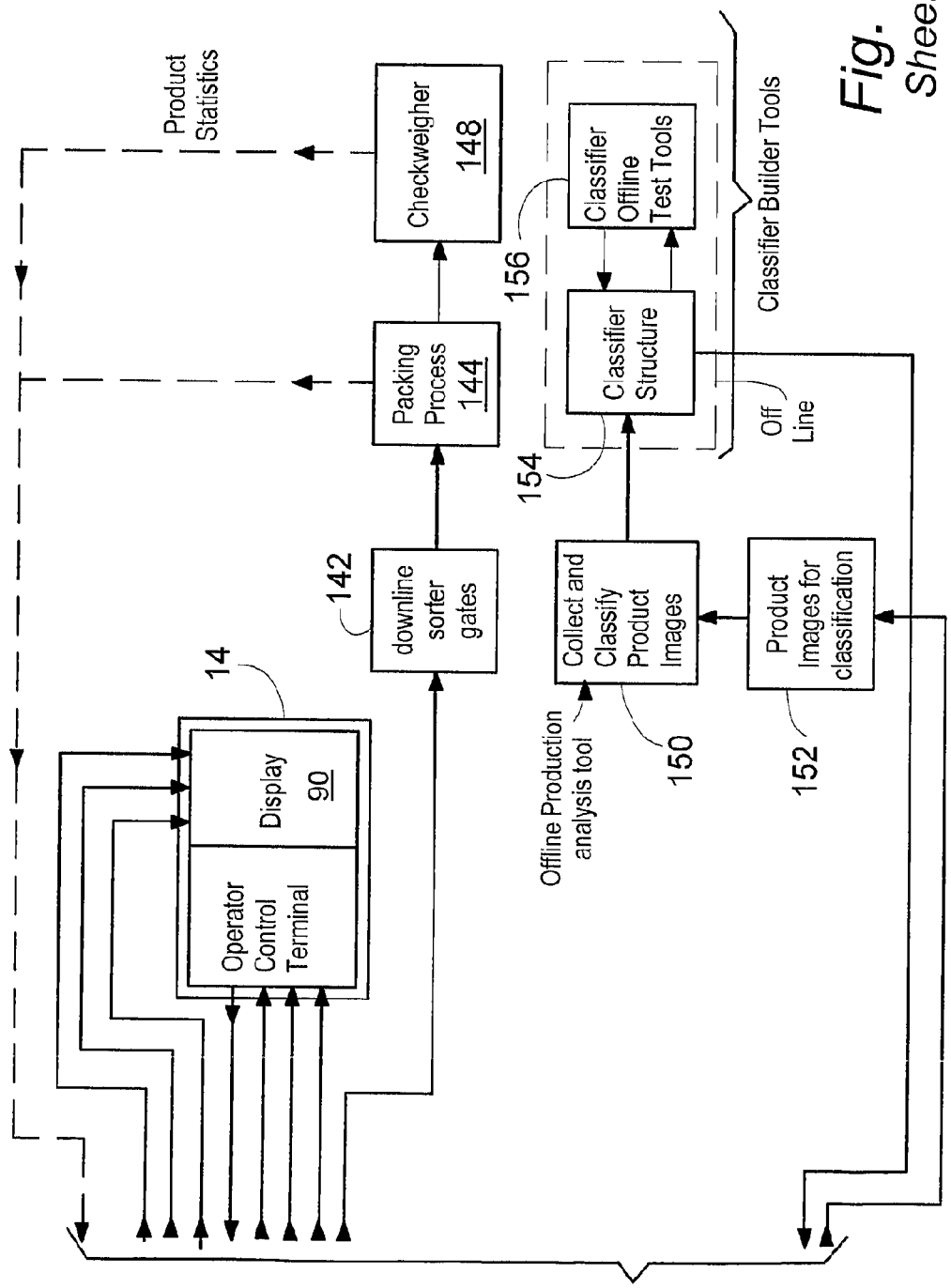
Fig. 10 Sheet 2

TWO COLOUR VISION SYSTEM

FIELD OF THE INVENTION

This invention concerns vision systems, especially vision systems as employed in food cutting and portioning apparatus.

BACKGROUND TO THE INVENTION

It is known to illuminate and view the end face of a length of foodstuff such as meat, using a video camera to obtain a video signal representation of visibly different regions in the end face, such a lean and fat regions, and to process the signal and compute for example the lean to fat ratio as well as the overall area of the end face.

The latter can be employed together with a density value for the foodstuff to compute the distance through which the foodstuff should be moved to enable a slice of a given weight to be cut from the length.

The lean to fat ratio can be compared with stored ratio values, to determine the quality of the portion, and this information can be used to direct the cut portion to one location or another, according to the lean/fat ratio which is usually a measure of the quality of the meat.

Difficulties have been experienced in accurately determining what in the camera field of view is product and what is supporting structure, so that the computation of the area is not always as accurate as it should be. Indeed a key difficulty in using vision systems to analyse product at the slicer cutting point is the acquisition of an accurate image and therefore video signal of the cut face of the product, clearly differentiated from the background to allow accurate image processing of the video signal and quantitative assessment of eg. fat to lean areas. This background may include parts of the machine itself, areas of product contamination and debris, and surface the product which is not part of the cut face.

This has been approached previously by offsetting light sources to the side or below the product, to place non-product cut face material in shadow, in an attempt to allow video signals relating to it to be excluded from video signals relating to the cut face, by thresholding the signal from the camera.

Other techniques have illuminated the sides of the product, casting the cut face in shadow, but this does not allow analysis of the cut face (eg to quantify lean to fat proportions of the cut face) which is now in shadow.

This allows the overall area of the cut face to be computed.

OBJECT OF THE INVENTION

It is an object of the present invention to provide an improved vision system which can be used to produce more accurate measurements of the end face of a length of foodstuff, especially meat, and in particular a more accurate measurement of the area of the end face and of the ratio of one constituent part of the foodstuff from at least one other constituent part thereof, when both are present in the end face.

It is also an object of the invention to provide a video signal from which the shape of the end face can be determined by reference to pre-stored shape data.

It is also an object of the invention to provide apparatus and methods by which data obtained by the improved vision system can be used to control the slicing and packaging of the sliced product.

SUMMARY OF THE INVENTION

According to one aspect of the invention there is provided a vision system for viewing the end face of product mounted in a machine which in use produces measurements relating to the area of the end face and of at least one constituent part of the product which is visible in the said end face and which comprises means for illuminating a region containing the end face and surrounding parts of the machine and scanning means for producing a video signal from an image of the illuminated region, wherein the region and end face of the product is illuminated by light of two predominantly different wavelengths characterised in that light of one wavelength is employed to generally uniformly illuminate the region, while light of the other wavelength is employed to produce a pattern of light at least on the product end face.

Preferably the light is obtained from two separate light sources.

Typically the light pattern extends over the whole area.

Typically the pattern is one of parallel spaced apart lines of light of the said other wavelength.

Typically the generally uniform illumination is performed using green or blue light, and the pattern is formed using red light.

Conveniently the green or blue source comprises an array of green or blue LEDs, or a filament or halogen lamp or array of white LED's with a green or blue filter placed between the lamp or the array and the region to be illuminated.

Preferably a laser light source is employed to create the pattern.

The laser source may form a part of a structured light generating head which in use produces a series of parallel straight lines of monochromatic light, typically red, typically equally spaced apart, on the product.

Preferably the scanning means comprises a video camera which produces the video signal.

In a preferred embodiment different components of the video signal corresponding to the two different wavelengths of illuminating light are separated by software into a first image signal comprising only signal corresponding to the pattern and into a second image signal comprising signal corresponding to the image produced by the illumination using the said one wavelength light.

Conveniently information on the extent of the end face is determined by processing an image signal derived from the first image signal.

Preferably memory means is provided for storing information on the components of the machine which in use extend into the field of view of the scanning means, and signals obtained from the stored information are employed to gate the video signal to exclude video signal corresponding to regions of the field view which are known not to contain any part of the product end face.

Preferably the angle the parallel lines make relative to the end face, is adjustable, so that the lines cross the end face at a specific given angle, and in general only those parts of the field of view of the scanning means which are crossed by lines of the appropriate wavelength, and which are at that given angle, will correspond to the end face of the product, while parallel lines in the field of view at other angles, indicate a region in the field of view which is not part of the end face of the product.

Conveniently the gating operates to exclude video signal of parallel lines crossing flat regions of the machine parallel to the end face of the product to leave a residual video signal composed of parallel lines only where they cross the end face of the product.

Signals defining an electronic mask to be used inter alia for video signal gating may be generated from the residual video signal, using image processing techniques. The mask also defines the size and shape of the product end face.

Alternatively points in the video signal at which the parallel lines change direction or disappear are determined using image processing techniques, and using a point joining algorithm these points can be joined by software to generate an electronic mask as aforesaid which can be employed for gating and equates to the size and shape of the product end face.

In a further preferred embodiment a source of white light is also provided whereby in use the whole of the region in the field view of the scanning means can be illuminated by white light and the scanning means is enabled to produce a full colour video signal of the region, and the mask is used to gate the full colour video signal to remove parts thereof which do not correspond to the product end face, to leave a full colour video signal of the end face alone.

The gated full colour video signal of the product end face is subjected to image processing software to identify signals of at least one particular colour.

Typically differently coloured regions of the product end face are distinguished by the software by reference to colour, and measurements using further software are performed on the signals corresponding to the differently coloured regions.

A vision system as aforesaid which produces an original full colour video signal may be used to scan the end face of a piece of meat containing lean and fat regions, and wherein signals relating to the latter are distinguished and separated from those relating to the former by colour and measurements made thereon to determine the size of lean and fat regions.

Where grey-level thresholding tools (software or hardware) are to be used to determine the different regions in the product end face, such as regions of lean (which will tend to be dark grey) and regions of fat (which will tend to be light grey or white) in a piece of meat, or cavities or discoloured regions in the end face of a piece of cheese, the colour video signal may be converted to a monochrome grey-level image signal to allow thresholding to be performed, and measurements are then performed on the thresholded signal and if appropriate also the original signal, using appropriate further software or hardware.

Software or hardware calliper tools may be employed to measure the height and/or width of the product end face, and/or of different visually distinguishable regions in the end face, and area values of the measured regions can be computed.

Typically the following dimensions of the end face of a meat product are obtained from the video signal, namely
Overall area of end face,
Area of lean meat in end face,
Height of end face,
Area of fat within the end face, and
Width of end face.

A ratio of lean to fat areas may be computed from the two area values.

A vision system as aforesaid may form part of a product slicing machine and the measurements and/or dimensional values are sent to a slicer controller, to control the thickness of the next slice to be cut.

In such a vision system the dimensional values may also be sent to slice and pack grade-level decision logic, to control down-line gates.

Where a monochrome grey scale video signal is produced, the latter may be sent to a feature classifier which in use is adapted to return an electronic flag to indicate whether or not a particular feature can be found in the video signal of the end face.

In such a vision system a state vector machine (SVM) based feature classifier may be employed and if a feature is found to be present, its dimensions are determined.

The invention is of particular use in assessing the end face of a side of bacon, and, in this event the classifier operates to determine if certain bacon muscle is present or not in the end face, and if so its dimensions are measured.

As previously mentioned, when the vision system forms part of a slicing machine for slicing a side of bacon the dimensional values may be sent to a slicer controller to control the thickness of the next slice of bacon to be cut.

According to another aspect of the invention, there is provided a method of assessing an end face of product which is to be sliced and routing the slice according to the assessment and which is viewed by a colour video camera set in front, but to one side of, the product end face, comprising the steps of:—

1) using substantially monochromatic light centred on a first wavelength, illuminating the camera field of view to form a first picture signal.

2) using substantially monochromatic light centred on a second wavelength forming a plurality of spaced apart parallel lines which as seen by the camera will appear to cross the camera field of view at an acute azimuth angle to the scanning direction of the camera.

3) selecting the different wavelengths so that video signal content produced by light of one wavelength is readily separable from video signal content produced by light of the other wavelength on the basis of colour or after conversion to a grey scale monochromatic signal, by reference to grey level.

4) selecting the position of the second wavelength source relative to the product end face so that the parallel lines of light in the camera field of view extend at one angle across the product end face, but at a different angle where they intersect a side or top surface of the product.

5) in a first signal processing step, processing the video signal so as to separate signal content produced by the first wavelength light from that produced by the second wavelength light so as to leave only signal content relating to the line image of the second wavelength light.

6) in a second processing step, identifying any part of the line image video signal content which relates to lines in the field of view which extend at the said one angle, and separating each such part from parts of the signal which relates to lines which extend at other angles, to leave as a residual line image signal only signal content which corresponds to lines in the field of view, which extend thereacross at the said one angle, and therefore identify the end face of the product.

7) generating an electronic mask from the residual line image signal which corresponds to the shape and size of the end face.

8) creating from the electronic mask a gating signal, and gating the video signal produced using the first wavelength light, so as to exclude therefrom all video signal content not coincident with the mask signal, to form a residual picture signal, corresponding only to the end face.

9) separating those parts of the residual picture signal which relate to lighter coloured (or lighter grey) regions of the end face, from those parts which relate to darker (or darker grey) regions of the end face, to leave a partial video signal relating only to one or the other type of region.

10) computing the total area of the end face from the residual picture signal or the mask, and the total area of the regions of the end face corresponding to the partial video signal, and 11) computing a grade value for the product from the area value of the end face and the area value from the partial video signal, and comparing the grade value with at least one preset numerical value, and directing a subsequently cut slice of the product to one or another of two or more collection points depending on the grade value computed for the end face of the product from which the slice has been cut.

If the separation step (9) is to be performed by grey level thresholding the colour video signal is converted to a monochrome grey level signal.

Where the video signal is a colour video signal the separation of step (9) can be performed on the basis of colour.

The invention also lies in the combination of a slicing machine a vision system as aforesaid when adapted to operate in accordance with the foregoing method.

The invention will now be described with reference to the accompanying drawings, in which:

FIG. 10 is a block schematic diagram of the vision system, video signal processing stage and controls for the machine of FIG. 1 et seq;

Figure 12:
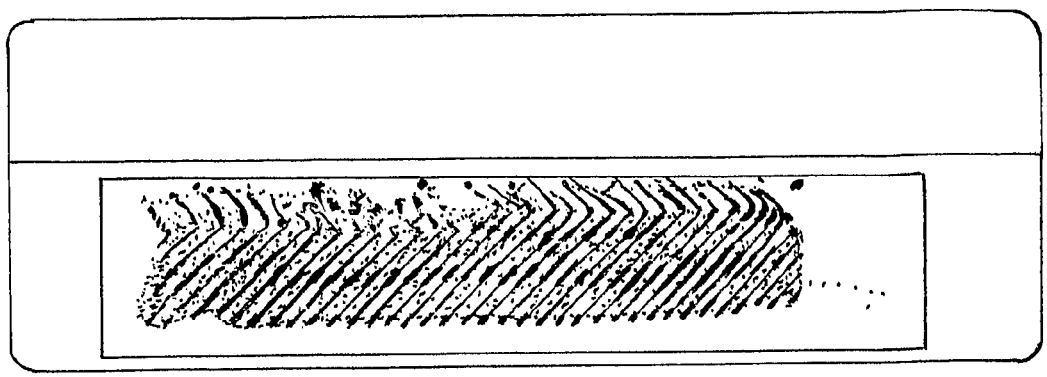
Figure 13:
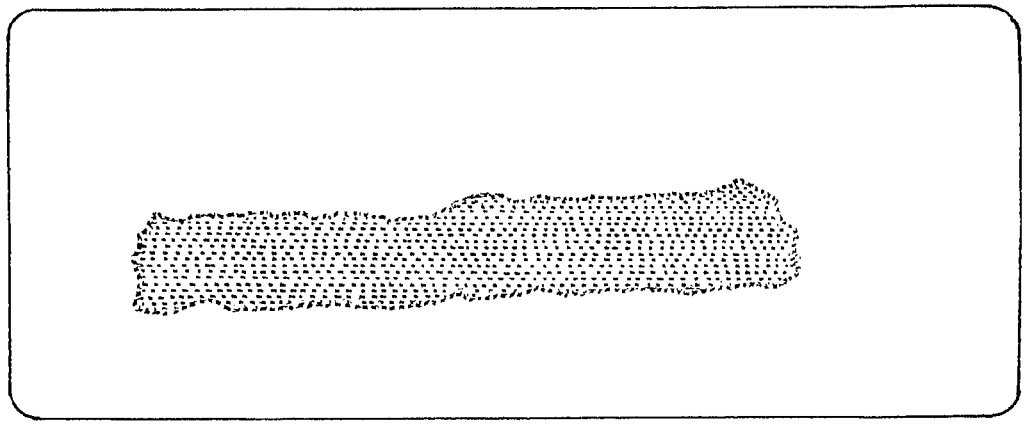
Figure 14:
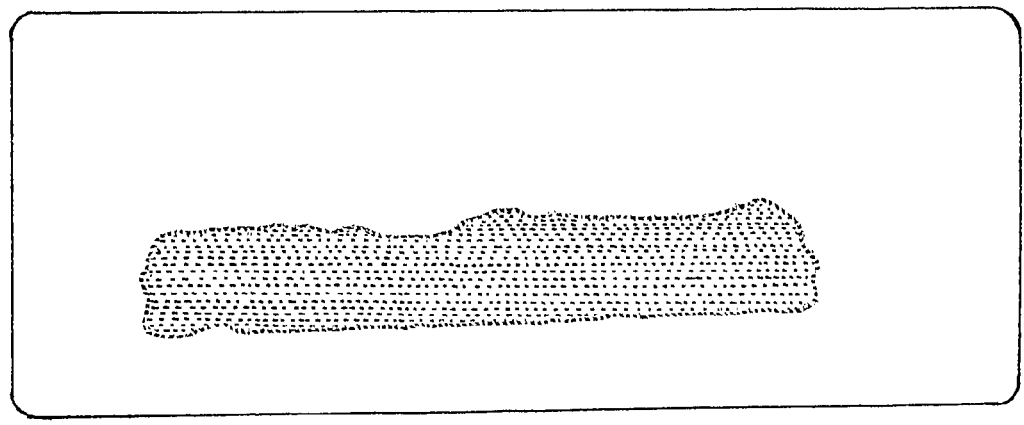
Figure 15:
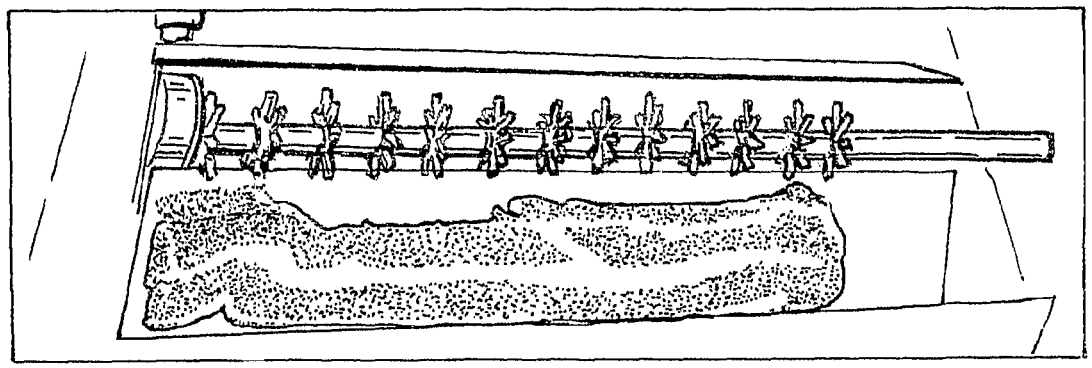
Figure 16:
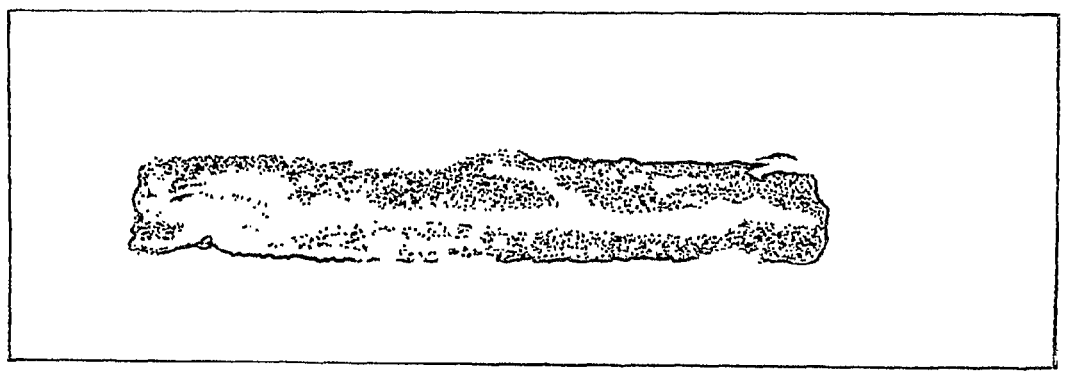

FIG. 12 is a screen display produced by image signal from a camera viewing a cut end face of a side of bacon at the end of a delivery conveyor with lines of red light crossing the cut end face at approximately 45° relative to the plane of the delivery conveyor, in which the camera image signal has been electronically gated to remove signal content of objects in the field of view of the camera but not in the immediate vicinity of the end face;

FIG. 13 is a screen display of the coarse mask which remains after thresholding the signal corresponding to the area crossed by the 45° lines, from the signal corresponding to the remainder of the end face image;

FIG. 14 is the image signal obtained by eroding and then dilating the signal producing the outline of FIG. 13, to remove small dark islands separated from the main region which is crossed by the 45° lines, to produce a final mask signal corresponding to the shape of the end face of the product;

FIG. 15 is a screen display showing the end face of a side of bacon on the delivery conveyor illuminated by green light;

FIG. 16 is a screen display of the signal remaining after the signal which produces the FIG. 15 image is gated by the red mask signal of FIG. 14, to allow the areas of the darker and lighter regions of the end face to be computed.

Figure 1:
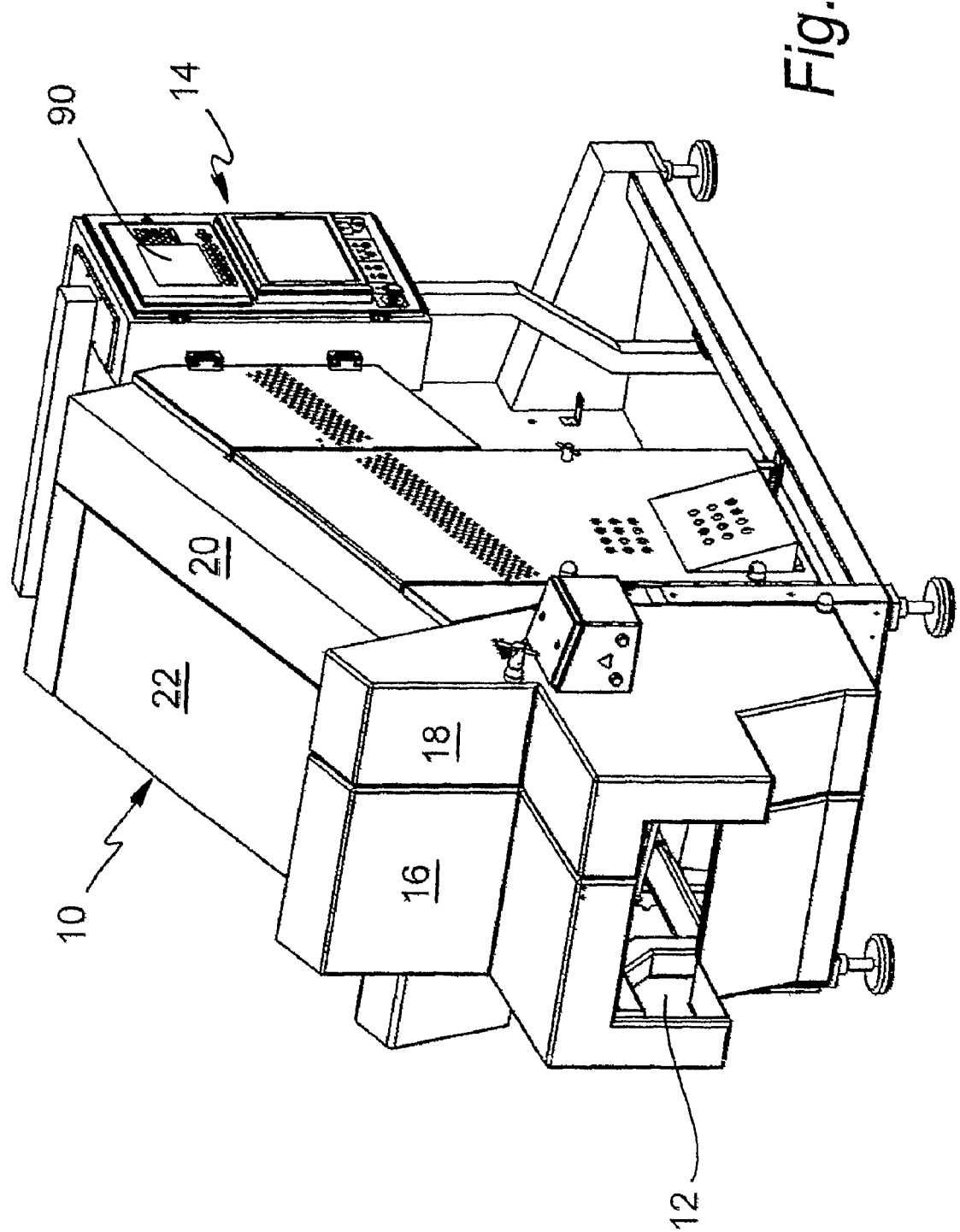
FIG. 1 is a perspective view of a slicing machine embodying the invention.

The slicing machine in FIG. 1 is shown with all the safety covers in place, and comprises a housing 10 within which an inclined product delivery conveyor (not shown) is located, a product exit 12 through which a collection conveyor (not shown) extends, onto which cut product is delivered, and a control panel 14. The covers are denoted by 16, 18, 20 and 22.

Figure 2:
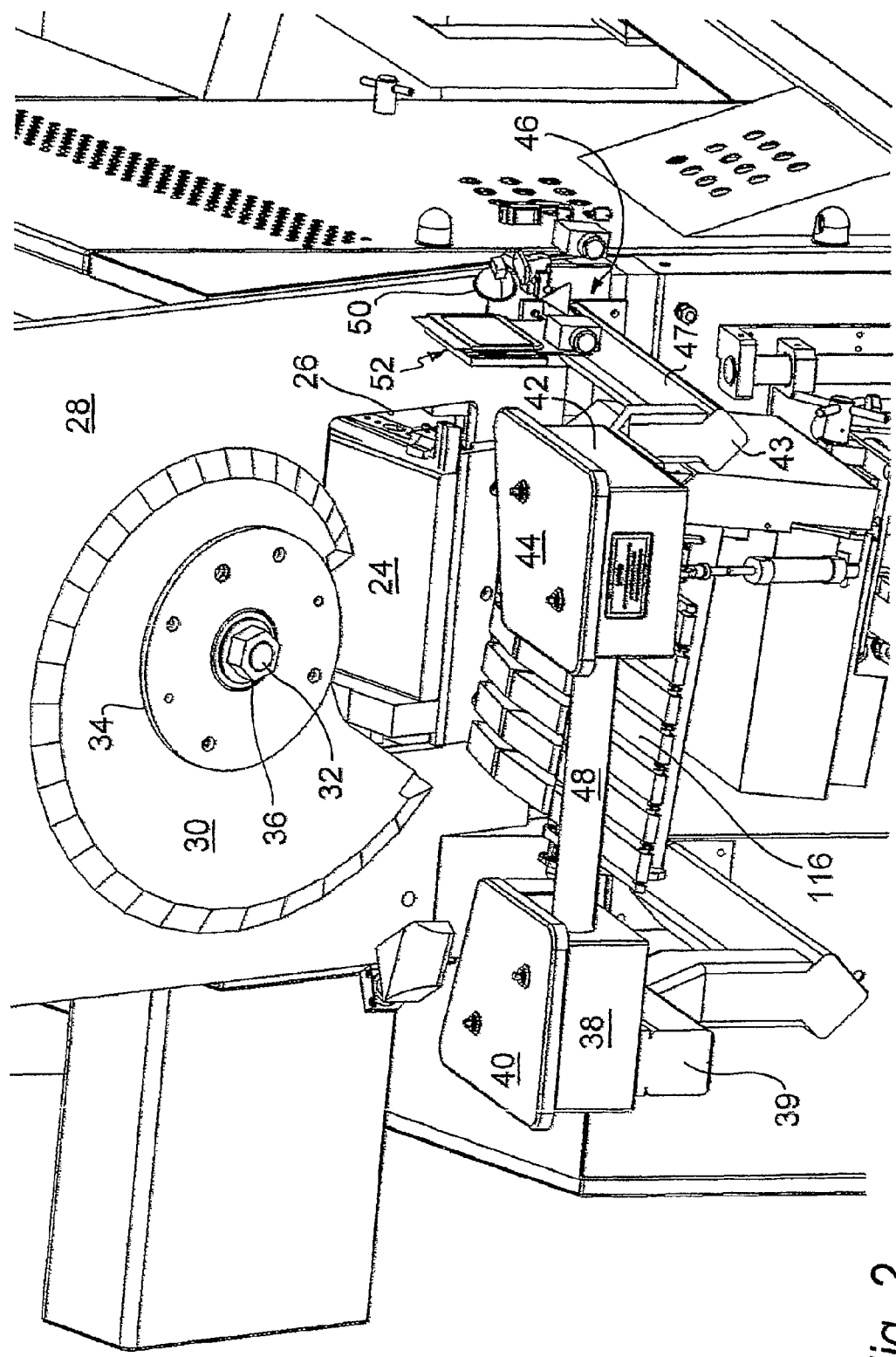
FIG. 2 is a perspective view to an enlarged scale of the cutting region of the machine of FIG. 1 with the safety covers removed showing the blade, delivery conveyor and a product collecting jump conveyor.

With covers 16 and 18 removed as in FIG. 2, the lower end of the inclined delivery conveyor 24 can be seen through an opening 26 in a plate 28 on which is mounted a slicing blade 30 which is rotated in use by a motor (not shown) mounted to the rear of the plate 28. The drive shaft is visible at 32 and the blade is located on the shaft in a conventional manner by being sandwiched between discs such as 34, and secured in place by a nut 36.

In front of, and to the left of the blade, is a camera housing 38 with removable cover 40, and in front and to the right is a laser housing 42 with a removable cover 44.

Also to the right of the blade and located nearer to the blade is a lamp assembly 46 for illuminating the lower end of the delivery conveyor 24.

The housings 38 and 42 are supported by frame members 39 and 43 and the lamp assembly 46 is carried by the cover 18.

Figure 3:
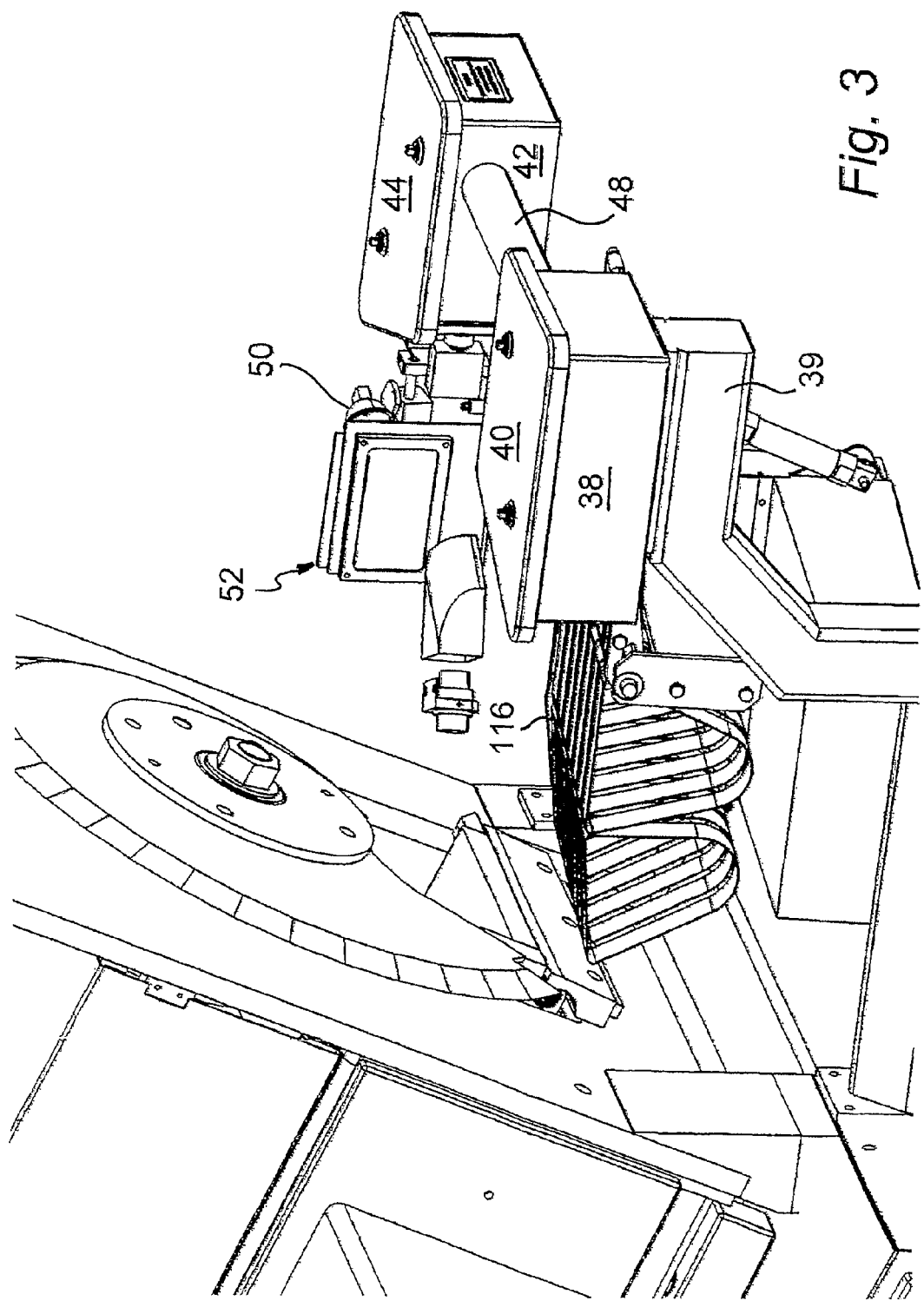
FIG. 3 is another perspective view of the cutting region from a different angle showing the laser housing, the camera housing and the illumination light source.

The two housings 38 and 42 are joined by a rigid arm 48 and the lamp can be seen at 50 in both of FIGS. 2 and 3.

Figure 4:
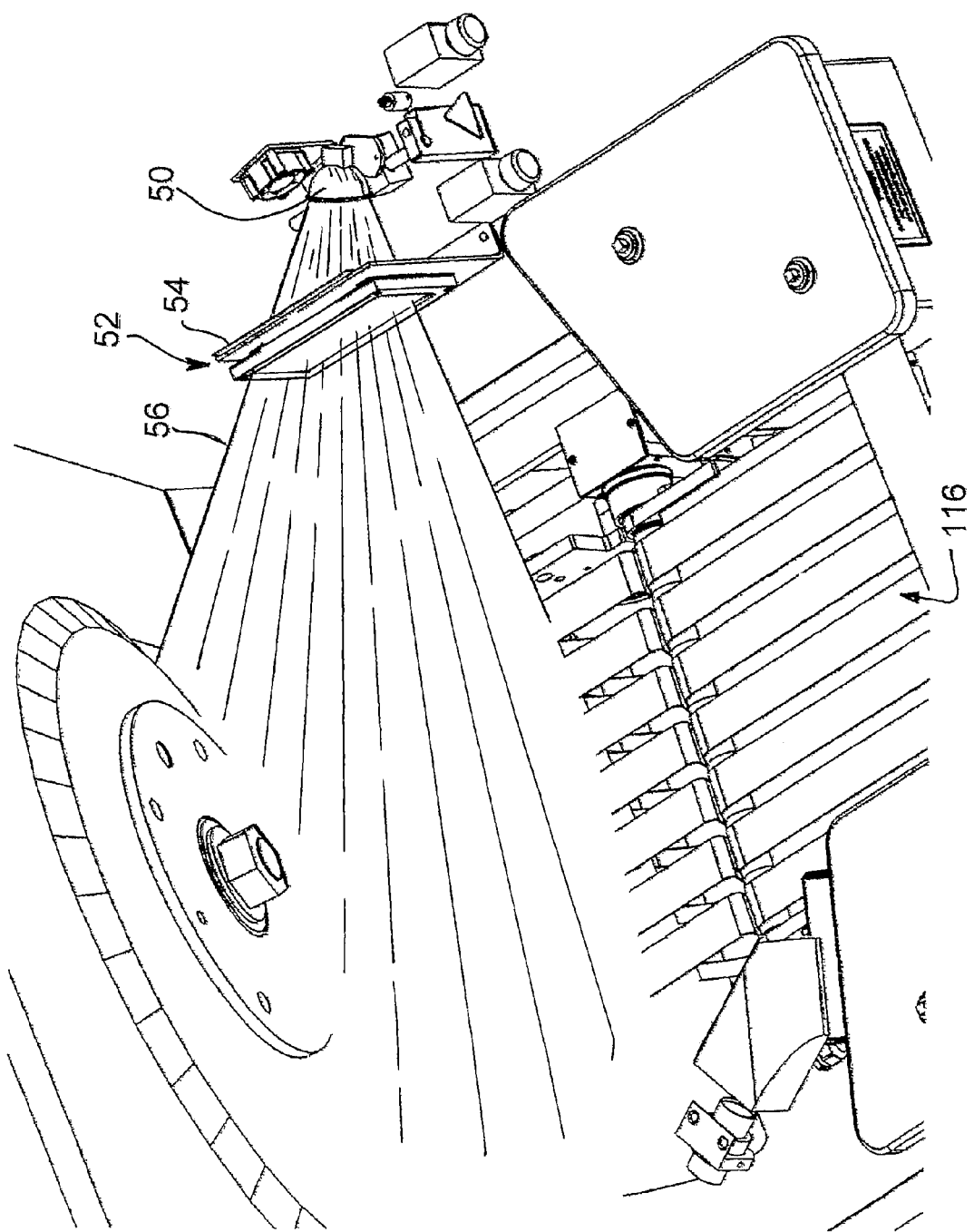
FIG. 4 is a further perspective view of the cutting region, from above, showing the extent to which the light from the illuminating light source will illuminate the blade and the cut end face of the product and the immediate environs of the blade.

In front of the lamp is a window assembly 52 which includes one or more filters such as 54 (see FIG. 4) so as to remove any red light wavelengths from the light passing through the window 52.

The lamp 50 may be a filament lamp but is more preferably a halogen bulb having an integral reflector which produces a diverging beam of generally white light. A filter can be employed to remove all wavelengths except green or blue light, so that the end face of the product will be illuminated by light whose wavelength is very different from that of the red end of the visible spectrum. The illumination can be seen emanating from the window, as a diverging beam 56.

Figure 5:
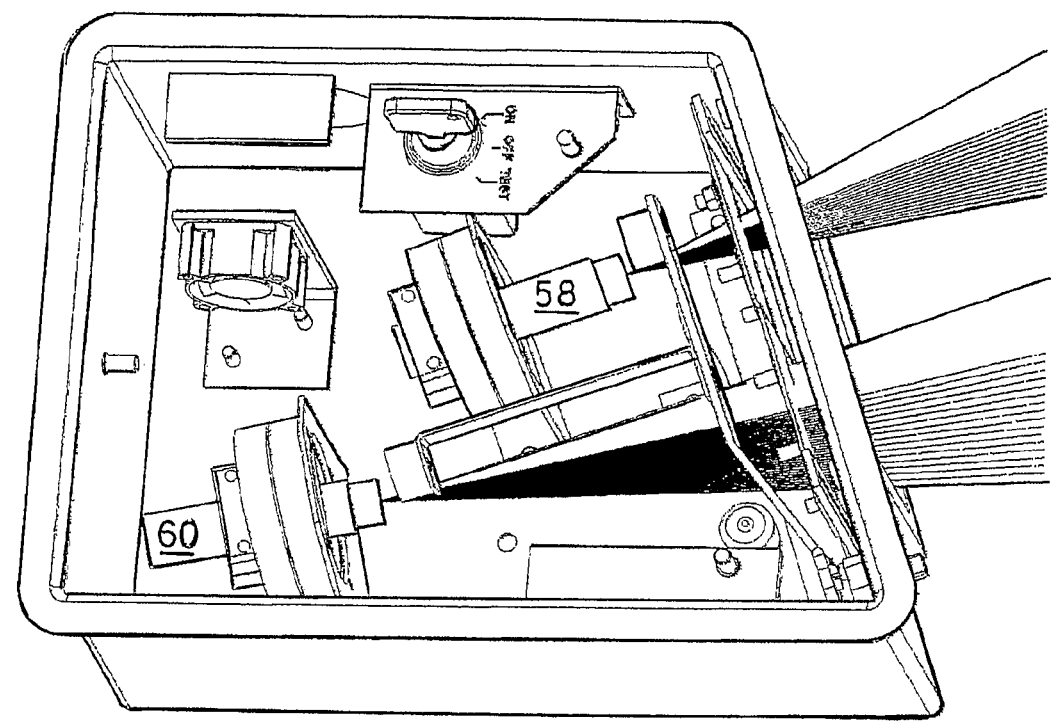
FIG. 5 is a view from above, with the cover removed, of the laser source.

Within the housing 42 are two red lasers 58, 60 best seen in FIG. 5. Each produces a slightly diverging beam of red light which is split into a plurality of parallel spaced apart thin lines of red light using an integral grating or mask.

Two lasers are used so as to produce a sufficient number of parallel lines across the field of view, to encompass the whole of the end face of the product, which as shown comprises a side of bacon. Other product could be lamb or pork which is to be sliced into steaks or chops, beef which is to be sliced into steaks or cheese which is to be sliced. The use of two lasers can result in supernumerary lines and these are masked by one or more plates in the housing 42, so that one pattern of lines from one laser can be positioned next to that from another laser without the supernumerary lines from one laser corrupting the pattern of lines from the adjacent laser.

Typically the two lasers produce 15° divergent beams and together produce a total of 66 lines, at a spacing of 5 nm on the product end face, in which the lines lie at 45° to the front end of the delivery conveyor (which corresponds to the plane of that conveyor at that point along its length, and which will normally extend generally horizontally).

However the number of lines, the spacing, the 45° angle and the number of lasers is a matter of design choice, and the invention is not limited to the illustrated arrangement of 2 lasers.

Figure 7:
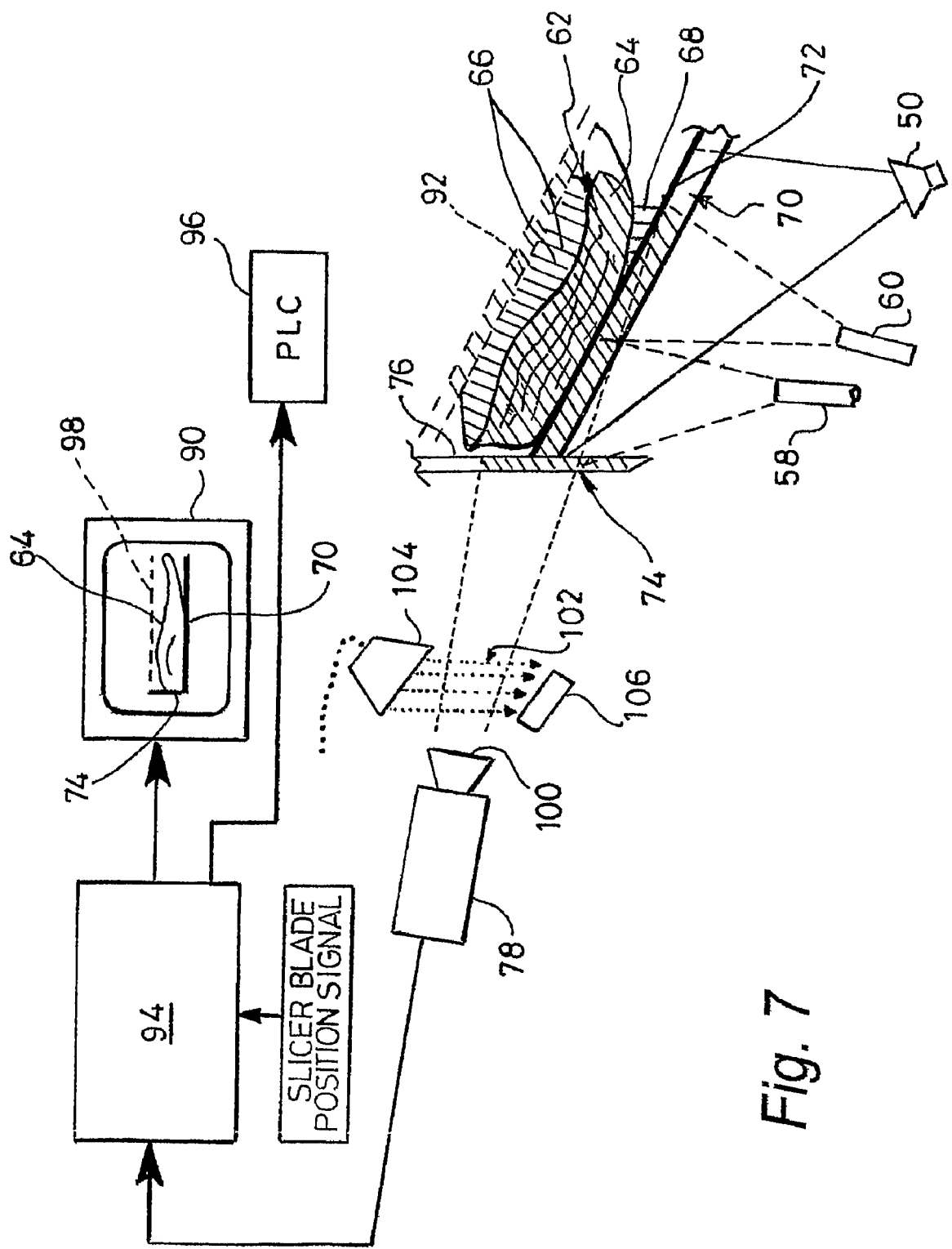
FIG. 7 is a diagrammatic illustration of how the laser source, illuminating light source and camera interact to provide signals for processing, and for display on a monitor screen.

By projecting the spaced apart parallel lines of light from the side of the product delivery conveyor at an angle towards the end face of the product which is generally perpendicular to the plane of the delivery conveyor, the lines will appear orientated at 45° on the end face. However, as shown in FIG. 12, as the lines of laser light leave the end face and begin to traverse the visible upper surface of the product, which is generally parallel to the plane of the delivery conveyor, and therefore at approximately 90° to the end face, they will change direction and trace a corresponding number of generally parallel lines at a rather different angle from that which the lines traverse the end face of the product. In FIG. 7 the end face of the product (typically a side of bacon) is denoted by 62 and the laser lines traversing the end face are denoted by 64, those traversing the upper surface of the product are denoted by 66 and those traversing the generally flat upper surface of the delivery conveyor by 68.

The exit end of the conveyor is protected by a plate 70 defining a straight edge 72 which also constitutes the shear plate for the blade 30. The left hand end of the conveyor (as viewed from the lasers) is defined by a plate 74 which defines a second straight edge 76 perpendicular to the edge 70, against which the left hand end of the product is abutted.

Figure 6:
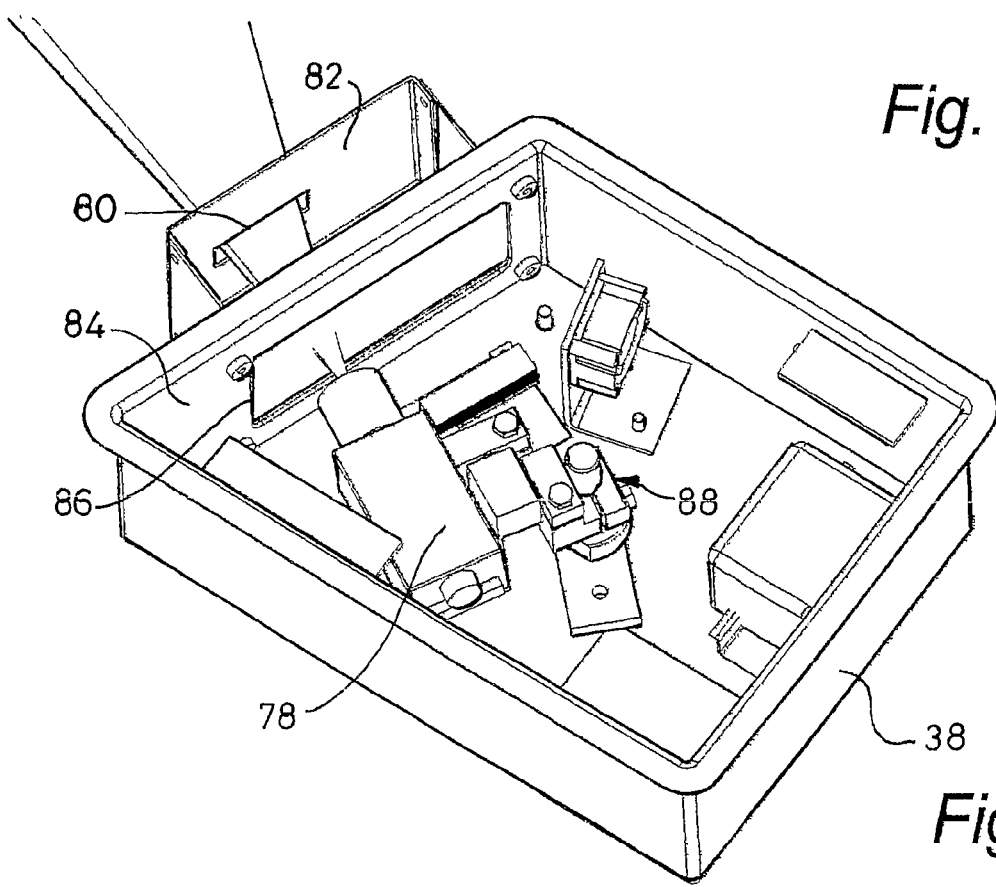
FIG. 6 is a view from above, with the cover removed, of the camera housing.

A camera 78 is shown in FIG. 6, located within 38, which views the illuminated region.

The straight edges 72 and 76 define the bottom and left hand edges of the field of view of interest (as seen by the camera 78), and its field of view is further delineated by an aperture 80 in a wall 82 located in front of the front wall 84 of the camera housing 38. The wall 84 also includes an aperture 86. The camera is adjustable in height, inclination and angle by being mounted about a 3-axis assembly generally designated 88.

The camera 78 is also shown in FIG. 7 and the view seen by the camera is shown in the screen display on the monitor 90 which forms part of the control panel 14, shown in FIG. 1. The displayed image shows the upright and transverse plates 74, 70 and the end face 64 of the product.

Typically a device such as an upper conveyor or thrust bar (shown in dotted outline at 92 in FIG. 7) overlies the upper surface of the product but terminates a short way back from the end face so as to be well clear of the path of the blade 30. Any such device will also present a face on which the laser light can form lines, and at least some of the end of the device can be generally parallel to the product end face 68, so that the red laser lines will traverse 92 at a generally similar angle of inclination as they traverse the end face 68. There is also a region to the right hand end of the product end face which may contain other parts of the machine which can produce spurious reflections of red laser light, some of which can be at a similar angle to that of those traversing the end face 68.

However it is possible to electronically gate out the signals in the video signal from the camera 78 in a vision computer and signal processing stage 94. The signals sent to monitor 90 are limited to those arising within a generally rectangular area defined by an electronically generated, generally rectangular window, shown dotted at 98 in FIG. 7. The left hand and bottom edges of the window are set to correspond to the straight edges 74 and 70. The upper and right hand edges are set manually, or automatically by window defining software or firmware in 94, relative to the left hand and bottom edges 76, 70.

Digital output signals from 94 are sent to a PLC 96 (in FIG. 7) and comprises a thickness signal with grade variable's such as height, width, lean fraction-muscle length. 94 and 96 will be described in more detail in relation to FIG. 10.

It will be appreciated that since plates 74 and 70 are fixed relative to the machine and therefore the camera 78, their x,y co-ordinates in the camera field of view will be constant, and the left hand and bottom edges of the window 98 can therefore be defined with reference to x and y co-ordinates within the photosensitive device (not shown) in the camera 78.

If the latter is read out on a pixel by pixel basis the x,y co-ordinates are definable by reference to the pixel matrix of the photosensitive device in the camera.

If the video signal is produced by line scanning at a constant scan rate, to allow different points on the photosensitive device to be defined by time lapse from the beginning of a scan, the x,y co-ordinates of the left hand and bottom edges 74, 70 (and therefore left hand and bottom edges of the window 98) can be defined in a similar time-related manner.

In a similar manner, the x,y co-ordinates of the top and right hand edges of the window 98 can be defined with reference to the pixel matrix, or by reference to lapsed time from the beginning of a scan.

The camera includes a lens 100.

In order to prevent spatter and debris produced as the product is cut by the blade 30, from obscuring the camera 78 or any window in front of the lens, a curtain of moving air 102 from a source 104 is created in front of the camera, and in particular in front of a polycarbonate protective window (not shown) located in front of the lens 100.

A heater 106 is also provided to warm the air in the region of the camera, to reduce condensation and prevent the lens or window 100 from misting up when the machine is operated in a low temperature environment, as may be required if the product is a foodstuff that needs to be kept below a particular temperature such as 4° C. or lower.

Where the product is not of uniform height from left to right (as in the case of bacon, lamb, pork or beefsteak) the product compressing device 92 may be adapted to follow the general trend of the product cross section, and in that event may extend across the camera field of view non-parallel to the straight edge defined by 70. In that event the upper edge of the window 98 may be adjusted either manually, or automatically within 94, so as to follow the inclination of 92. Alternatively a further smaller window may be electronically generated, typically within 94, in which the upper edge is inclined relative to the lower edge, so as to correspond to the inclination of 92, and the signals released by the first window are gated by the further smaller window.

Figure 8:
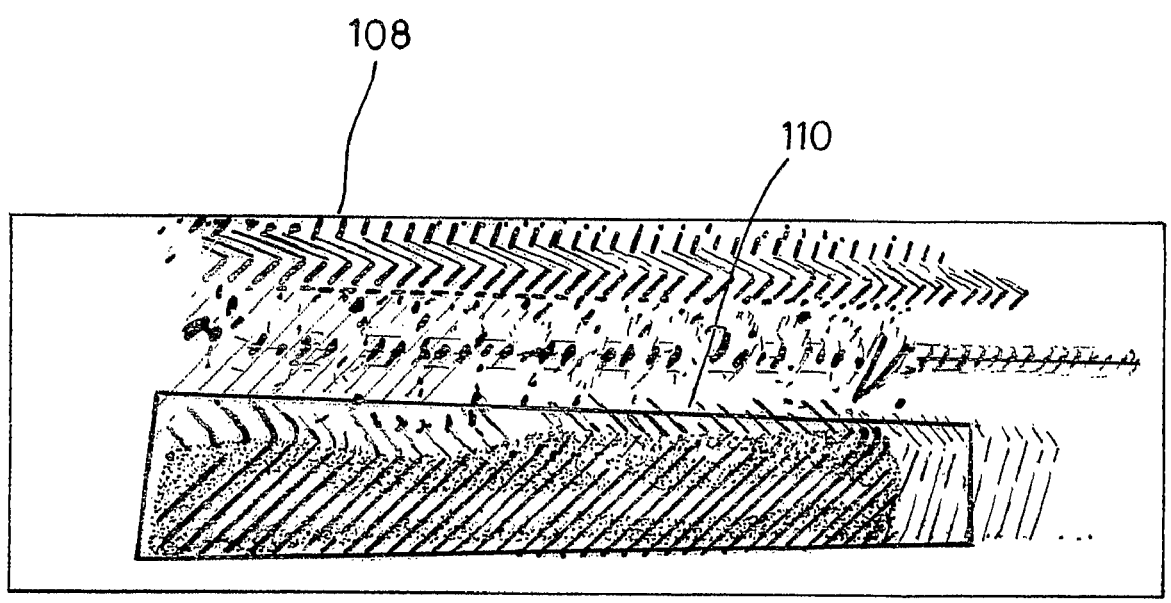
FIG. 8 illustrates one of the screen displays which can be obtained on the monitor.

The effect of the further smaller window can be seen in FIG. 8, in which the generally rectangular primary window is designated by 108 and the further window by the slanting upper edge of the outline 110, in the screen shot of a display on the monitor 90.

Figure 9:
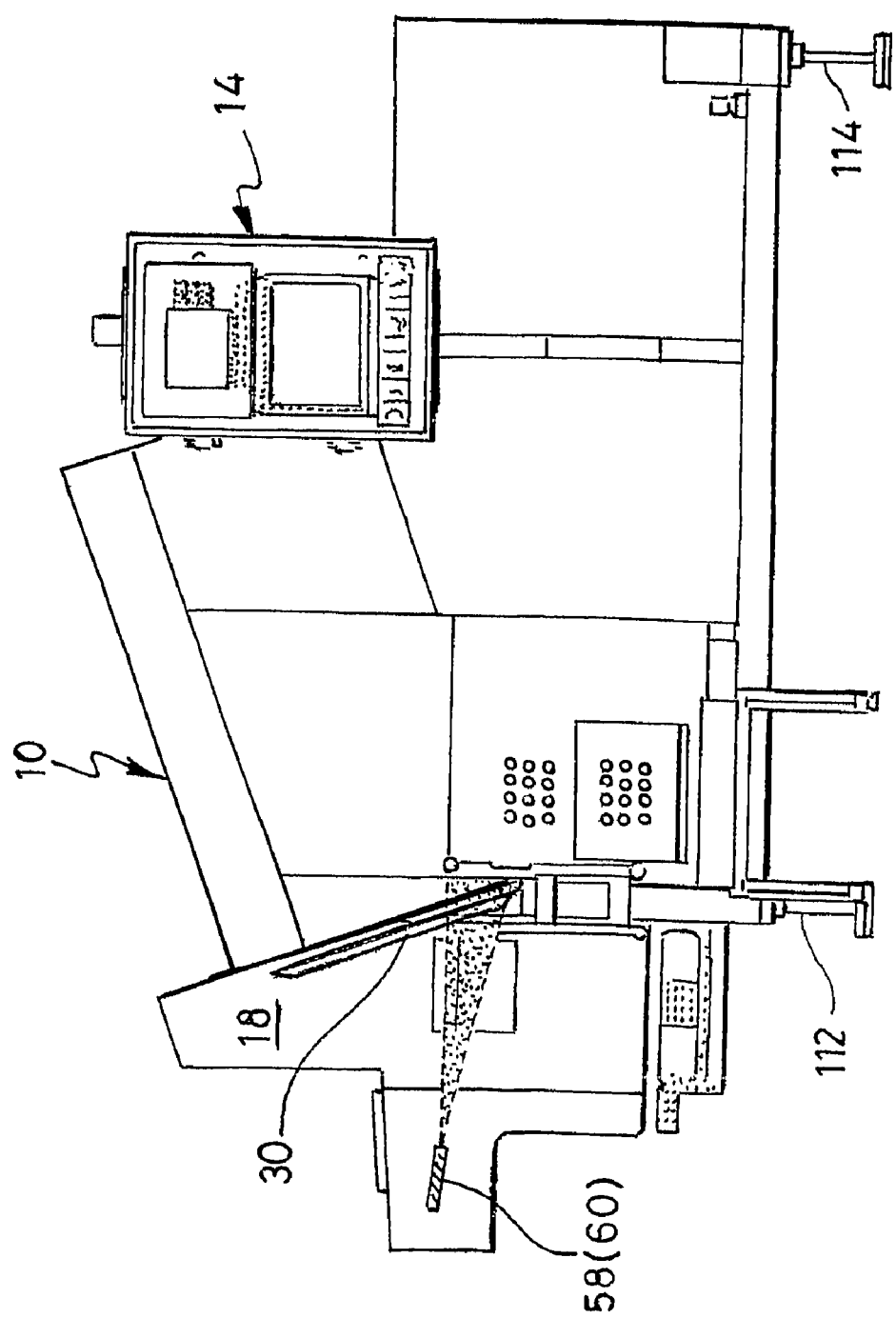
FIG. 9 is a side elevation of the machine shown in FIG. 1 and shows the general position of the lasers.

FIG. 9 shows diagrammatically the inclination of the delivery conveyor housing 10, the position of the lasers 58, 60 and the blade 30, and of adjustable feet 112, 114 by which the machine can be levelled, and/or raised or lowered. This allows it to be aligned with an exit conveyor (not shown) which accepts cut product from a jump conveyor 116 (see FIGS. 2, 3 and 4) onto which slices of product fall after being severed from the leading end of the product on the delivery conveyor. A jump conveyor is described in U.S. Pat. No. 5,125,303.

The described system allows full illumination of the end face without the need for complex lighting arrangements. The illumination can be from a white light source, a monochrome source or from two or more sources of differing colour to obtain good contrast between different features of different types of product.

In particular, by using a laser wavelength which is very different from the wavelength light used to generally illuminate the end face, it can be differentiated from the remainder of the field of view, and video signals relating to the end face are separated readily from video signals relating to the rest of the field of view, to provide signals on which image processing can be performed to assist in identification and quantification of features within the cut face.

The face of the product is protected from sources of light other than those described above in order to produce the clearest possible images. This is conveniently achieved by the covers such as 16,18 and slicer guards (not designated) which enclose the containing the product delivery conveyor and the camera and light sources.

In the slicer control system of FIG. 10, images of the product are captured, ideally by the system which will be determining the slice thickness and thereafter doing the grading. A camera may be located in a position which is close to where the slicing is to occur to obtain images which are close enough to the slicing station to start a classification process.

The camera 78 provides images to a signal pre-processor 118 for supply to a vision computer 120 (all of which make up 94 in FIG. 7). This includes a frame grabber 122 and performs separation by colour to produce Red and Green image data in 124 and 126. Signals are grabbed in response to trigger signals from the sensor 128 which in turn is triggered by the rotation of the blade 30.

A gating device 121 is controlled by signals from a control unit 123 which in turn is controlled by data from a memory device 125, which is triggered to release data stored therein by signals from the blade sensor 128 using the camera readout scan as a timebase synchronising signal. The operator control terminal 14 may used to enter the data in the memory device corresponding to the size and position of fixed objects such as machine and delivery conveyor parts in the camera field of view. Alternatively the data may be obtained from an image signal from the camera 78 when set to view only the end of the delivery conveyor when no product is present. In either case the data is such that when read out in synchronism with the blade rotation and the camera readout, it can be employed via 123 to inhibit image signals relating to the fixed objects from reaching the Red image signal processor 124.

Appropriately positioning 128 ensures that the camera only images the end face 68 when the blade 30 is clear of the face 68, as shown in FIG. 2.

The green image signals in 126 are gated by an electronic mask/gating signal obtained from 124 to leave only image signals of the product cut face. These are then analysed further in 130 to measure the area of fat and the area of lean. Mean density values for fat and lean meat together with the fat and lean area measurements may be used to calculate in 130 the thickness to which a slice must be cut to give a particular weight. Module 134 forms part of the PLC 96 of FIG. 7, and provides signals to servo amplifiers 136 to control servo motors 132 which control each slice thickness.

The height, width and lean fraction of the end face are determined from the parameters of the end face area image signals in a feature classifier 138. Signals from 138 pass to 134 and also to other logic in 140. This determines whether a desired feature is present in the image of the end face and if so what its key dimensions are using vision processing calliper tools. The values of these key dimensions allow a grading of the next slice, and the grade decision is passed to an array of gates 142 to control the delivery of the next slice to be cut, to an appropriate packing station 144.

The logic 140 compares the grade information from 138 with a series of pre-set thresholds for each parameter. Depending on the pre-set threshold settings, the slice (or a pack which is to contain two or more slices) is tagged as a reject, or a Grade A, B or C etc, and is diverted into the appropriate packing station(s) which process that grade of product.

Reject statistics are compiled in 141.

Data classification has been one of the important elements in the growing field of Artificial Intelligence (AI) and machine learning. In the general case the machine is presented with a set of inputs that represent some data point, and is asked to suggest an output (classification) based on a set of pre-stored conclusions (information usually referred to as a knowledge base).

Perhaps the most important feature of any classification algorithm in the realm of machine-learning is its ability to build a "knowledge-base," based on a set of training data, or in other words, to learn. A training data set may for example encompass thousands of images (the inputs) which are pre-classified (by a human operator) in an off-line procedure, into different score-groups (the outputs). Using a method known as supervised learning, the algorithm parses all of these input/output pairs and attempts to determine (ie to "learn") the function that appropriately maps the inputs onto their corresponding outputs. Using a formal learning method, it builds some knowledge that is based on the training set which can later be used to classify other data into sets. Usually characteristics (known as vectors) of the inputs are identified as determining the particular score for any input, and these vectors are looked for in the future inputs.

In the realm of supervised learning algorithms, there are many options. Neural Network and State Vector Machine (SVM) systems have been successfully implemented and enjoy widespread use. SVM's appear to have very good generalisation behaviour, which is a learning machines ability to draw conclusions from learning samples and apply them to other pattern instances, which it has never seen before.

An SVM based system is employed in the off-line classifier incorporated into the present system of FIG. 10. The preferred SVM based system is the MANTO system (particularly MANTO 2) as developed and supplied by Stemmer Imaging of Germany.

At the heart of the MANTO system there are two components: One is a non-linear multi-resolution filter (MRF) for image-preprocessing, which detects relevant features at different scales and transforms image information into a feature vector. The other ingredient is a learning and pattern classification algorithm, based on the technology of support vector machines (SVMs), as has been developed at various universities and research laboratories.

The MANTO system recognises an image pattern by first applying an MRF to the image and then feeding the resulting feature vector into SVM, which then decides on class membership and quality. The knowledge which enables MANTO to do this is contained in a data-structure called the MANTO-classifier (MCF), which contains the MRF parameters and the knowledge obtained by training from lists of learning samples. MANTO 2 allows the classifier to determine and express how nearly an image represents an instance of particular classification (regression). A probability can be given to this, producing a sliding scale for the feature property of interest. e.g. if a bacon muscle is between 75 mm and 100 mm long, but nearer 100 mm, the MANTO 2 system might assess its length as 92 nm.

To this end threshold values for the comparators and logic in 140 are obtained using state vector machine (SVM) techniques. In particular 138 comprises a state vector machine (SVM) based feature classifier. This allows images to be classified according to the presence or absence of feature(s) (vectors) of interest, and further classified according to the properties and dimensions of feature(s) of interest, eg the shape of the end face and/or of the length of a particular individual, region common to the end faces, such as a region of muscle in bacon.

The grade attributable to a slice to be cut, obtained from 138, may be used to direct the slice thickness calculation in 134 such that one grade of product is sliced at a different thickness from other grades. This would generate, as an example, differing fixed weight slices or packs, for different grades of product.

Items 150, 152, 154 and 156 comprise a suite of off-line classifier building and testing tools which assists with the classification, in that a person can perform a classification visually, and identify whether a desired feature is present or not. If the feature is present, a line can be drawn on the screen image showing a dimension of the feature, using a mouse or tracker ball device. The length of the line is measured and recorded in 150 and 154. The image signals can be scaled to real world dimensions so that the length extracted from the drawn line can be displayed and saved in conventional units of length with an image of the product end face on which the measurement has been made.

Collection of data from specimen product end faces is undertaken prior to operation of the machine, and can be done on initial installation and left, or performed when the machine is to be used to slice a new batch of product, or completely different product.

A check on the decision-making accuracy of 138 can be performed off-line by running a software program to present data of previously classified images in 150 to classifier logic in 154 in order to analyse its performance. Batches of images can be processed to produce statistics on the classifier accuracy.

The system shown in FIG. 10 also includes a grading supervisor module 146. This is supplied with data from 144 and a check weigher 148 so as thereby to monitor the numbers of product slices or packs being classified into each grade. The grade acceptance thresholds in 140 are controlled by 146 which in turn can be altered by signals from the control terminal 14 so as to override neural classifier produced criteria, so that a constant throughput can be maintained if desired, whereby a given grade will always be the same percentage of the overall output. In this way minor variations in input product characteristics will not result in increased percentages of slices or packs graded as rejected or a lower grade. Using such a technique, the acceptance thresholds can be adjusted so that for example a similar percentage of product will be placed into each grade category irrespective of the actual input quality, and the properties of each grade will change according to the properties of the input material.

Product end-face image data from the frame grabber 122 is not only supplied to 124 and 126, but is also available for storing as a plurality of classified images in a product analysis tool 150 which collects and classifies product images from 122. Image files of differently classified product end faces are stored in 150, with the related feature classification information. A classifier structure control tool 154 determines parameters by which image signals relating to end face parameters can be classified by 138 and supplies these to 138. Product grade is determined in 138 and the grade information is sent to the grade threshold and comparator logic 140. The output from 140 comprises product grade command information for controlling sorter gates for cut product, as previously described.

The classifier structure control tool, 154 also provides data for off-line software testing by 156. Pre-classified images, can be used in 156 to optimise the classifier rules in 154 to in turn alter grade determination by 138. The threshold data in 140 can therefore be updated fully automatically without operator intervention or manually by allowing operator input commands from 14 to override data stored in 140 in response to statistics displayed by 14 (typically but not exclusively by the monitor 90) to the operator. These could show that an inappropriate set of thresholds is being employed in 140 following a change of circumstances, or input product, or customer requirements.

Figure 11:
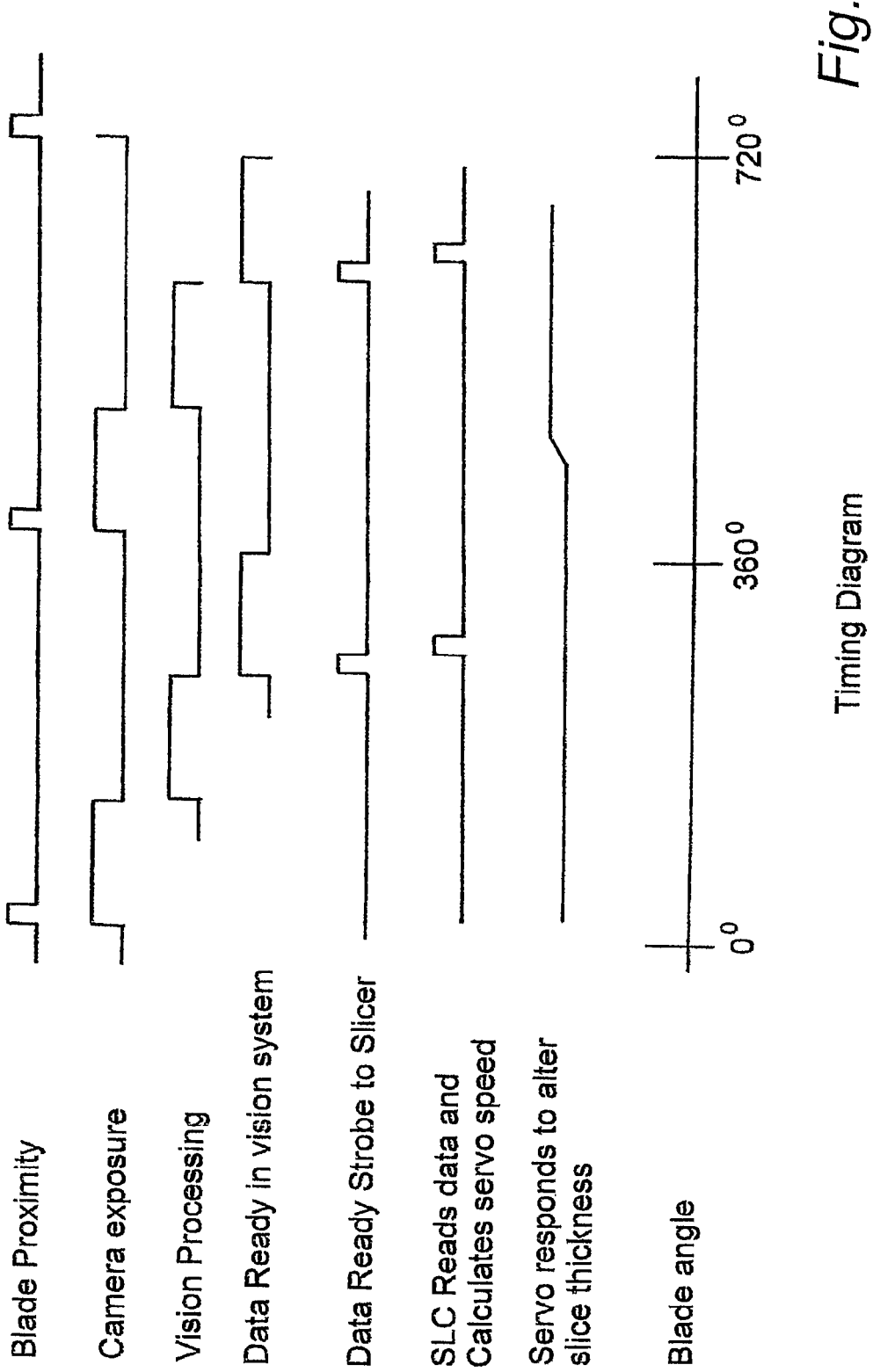
FIG. 11 is a timing diagram which should be read in conjunction with FIG. 10.

FIG. 11 shows the occurrence of camera operation and signal processing events in relation to blade position. Where the machine operates to deliver the product to the cutting station at a constant rate, the slice thickness is controllable by altering the time delay between cuts. This may be easily achieved by driving the blade 30 through a variable speed drive, and slowing down or speeding up the blade after a cut has been made, so that more or less of the product has been advanced into the path of the blade before the latter next enters the product.

Where the blade speed is not controllable the thickness adjustment is made by speeding up or slowing down the delivery conveyor, so that more or less product has been advanced through the cutting plane before the next cut is made.

The present invention is applicable to either technique, but the latter is the preferred one.

From FIG. 11 it will be seen that the high speed data capture and processing is possible using a CCD camera and a high speed computer. This can enable a decision on slice thickness to be made in the time interval after the blade 30 leaves the product and before it has rotated to the position at which it will next enter the product.

FIGS. 12 to 16 illustrate what will be seen by the operator on the monitor display 90 depending on which stage of processing the video signal is derived from for display, and FIG. 12 shows the red image before processing by 124 to exclude non-45° red lines, FIG. 13 shows an intermediate stage in 124 after thresholding the video signal of FIG. 12, FIG. 14 shows the output from 124 after eroding the signal of FIG. 13 to remove small unconnected detail and dilating the resulting signal to merge the components into a single monochrome shape, corresponding to the shape of the end face of the product, so as to exclude any extraneous features from the image, FIG. 15 shows the original colour picture image without any processing.

FIG. 16 shows the result of gating the signal of FIG. 15 with a window or mask generated from the signal of FIG. 14 and thresholding so as to convert to white those parts of the video signal which relate to light coloured regions of the signal of FIG. 15, and to convert to black, those parts of the video signal which relate to grey regions in FIG. 15. This thereby yields a two phase representation of the end face, in which lean regions of the product are black and fat regions are white. The lean regions can be quantified by appropriate processing of the "black" signal content of the signal producing the FIG. 16 display.

If the area of fat is required the signal producing FIG. 16 can be inverted so that lean regions are white and fat appears as black, and the black area quantified by appropriate processing of the black signal content of the inverted signal.

The area of the whole of the end face can be obtained by adding the computed area value of lean to the computed area value of value fat.

The proportion of lean to overall area can be calculated by comparing the lean area value with the total computed area value.

The value of lean to fat is calculable by comparing the area value of lean to the area value of fat.

The height and width of the end face in FIG. 16 can be measured by conventional image calliper processing in 138. The results can be sent to 140 for grade threshold comparison, as described above.

The invention claimed is:

1. A slicing machine for cutting slices from an end face of a food product mounted in the machine, wherein the machine includes a vision system arranged to view the end face during slicing and produce measurements relating to the area of the end face and of at least one constituent part of the product which is visible in the end face, and the vision system includes:
    an illumination arrangement for illuminating a region containing the end face with light of two different wavelengths; and
    a photosensitive device for producing a video signal representing an image of the illuminated region,
    wherein light of one wavelength is employed to generally uniformly illuminate the region, while light of the other wavelength is employed to produce a pattern of spaced apart parallel lines of light at least on the product end face, and
    the vision system is arranged to separate different components of the video signal corresponding to the two different wavelengths of illuminating light into a first image signal comprising only signal corresponding to the pattern and a second image signal comprising signal corresponding to the image produced by the generally uniform illumination, to determine information on the extent of the end face by processing the first image signal, to use this information to generate an electronic mask and to gate the second image signal using the electronic mask to leave a residual picture signal corresponding to the end face alone.

2. A slicing machine as claimed in claim 1 wherein a laser light source is employed to create the pattern.

3. A slicing machine as claimed in claim 2 wherein the laser source forms a part of a structured light generating head for producing a series of parallel straight lines of red light, equally spaced apart, on the product.

4. A slicing machine as claimed in claim 1 wherein the photosensitive device is a video camera which produces the video signal.

5. A slicing machine as claimed in claim 1 wherein the angle the parallel lines make on the end face is adjustable so that the lines cross the end face at a specific given angle and in general only those parts of the field of view of the photosensitive device which are crossed by lines of the appropriate wavelength and which are at that given angle will correspond to the end face of the product, while parallel lines in the field of view at other angles indicate a region in the field of view which is not part of the end face of the product.

6. A slicing machine as claimed in claim 5 wherein points in the video signal at which the parallel lines change direction or disappear are determined using image processing techniques, and using a point joining algorithm these points are joined by software to generate an electronic mask to be employed for gating purposes and which equates to the product end face.

7. A slicing machine as claimed in claim 6 further comprising a source of white light for illuminating the whole of the region in the field view, wherein the photosensitive device is able to produce a full colour video signal of the region, and the mask is used to gate the full colour video signal to remove parts thereof which do not correspond to the end face to leave a full colour video signal of the end face alone.

8. A slicing machine as claimed in claim 7 wherein the gated full colour video signal of the product end face is subjected to image processing software to identify signals corresponding to at least one particular colour.

9. A slicing machine as claimed in claim 8 wherein differently coloured regions of the product end face are distinguished by the software by reference to colour, and measurements using further software are performed on the signals corresponding to the differently coloured regions.

10. A slicing machine as claimed in claim 9 including a slicer controller, wherein measurements are sent to the slicer controller to control the thickness of the next slice to be cut.

11. A slicing machine as claimed in claim 7 wherein the colour signal is converted to a monochrome grey-level image signal, and software or hardware grey level thresholding tools are employed to separate signals according to grey level.

12. A slicing machine as claimed in claim 1 wherein a video signal is sent to a feature classifier which in use is adapted to return an electronic flag to indicate whether or not a particular feature can be found in the end face.

13. A slicing machine as claimed in claim 12 wherein a state vector machine (SVM) based feature classifier is employed and if a feature is found to be present, its dimensions are determined.

14. A slicing machine as claimed in claim 13 including a slicer controller, wherein the dimensional values are sent to the slicer controller to control the thickness of the next slice to be cut.

15. A method of assessing an end face of a food product mounted in a slicing machine arranged to cut slices from the end face, to produce measurements relating to the area of the end face and of at least one constituent part of the product which is visible in the end face, comprising the steps of:
    illuminating generally uniformly a region containing the end face with light of a first wavelength;
    producing a pattern of spaced apart parallel lines across the region with light of a second, different wavelength;
    producing a video signal representing an image of the region;
    separating different components of the video signal corresponding to the two different wavelengths of illuminating light into a first image signal comprising only signal corresponding to the pattern and a second image signal comprising signal corresponding to the image produced by the generally uniform illumination;
    determining information on the extent of the end face by processing the first image signal, and using this information to generate an electronic mask and to gate the second image signal using the electronic mask to leave a residual picture signal corresponding to the end face alone.

* * * * *